United States Patent
Wang et al.

(10) Patent No.: US 10,736,559 B2
(45) Date of Patent: *Aug. 11, 2020

(54) METHOD AND APPARATUS FOR ESTIMATING AREA OR VOLUME OF OBJECT OF INTEREST FROM GASTROINTESTINAL IMAGES

(71) Applicant: CapsoVision, Inc., Saratoga, CA (US)

(72) Inventors: Kang-Huai Wang, Saratoga, CA (US); Mark Hadley, Los Altos, CA (US); Chenyu Wu, Sunnyvale, CA (US)

(73) Assignee: CAPSOVISION INC, Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/544,110

(22) Filed: Aug. 19, 2019

(65) Prior Publication Data

US 2019/0374155 A1    Dec. 12, 2019

Related U.S. Application Data

(63) Continuation-in-part of application No. 16/416,266, filed on May 20, 2019, now Pat. No. 10,580,157, (Continued)

(51) Int. Cl.
*A62B 1/04* (2006.01)
*A61B 5/00* (2006.01)
(Continued)

(52) U.S. Cl.
CPC ............ *A61B 5/4255* (2013.01); *A61B 1/041* (2013.01); *A61B 5/1073* (2013.01); *A61B 5/1076* (2013.01); *A61B 5/1079* (2013.01); *G06T 7/0012* (2013.01); *G06T 7/12* (2017.01); *G06T 7/62* (2017.01); *G06T 2207/10068* (2013.01); *G06T 2207/30032* (2013.01); *G06T 2207/30096* (2013.01)

(58) Field of Classification Search
USPC ......................................................... 348/65
See application file for complete search history.

(56) References Cited

U.S. PATENT DOCUMENTS 7,983,458 B2    7/2011 Wang
10,346,978 B2 *  7/2019 Wang ........................ G06T 7/62
(Continued)

FOREIGN PATENT DOCUMENTS

WO    WO 03/053241 A2    7/2003

*Primary Examiner* — Behrooz M Senfi
(74) *Attorney, Agent, or Firm* — Blairtech Solution LLC

(57) ABSTRACT

A method and apparatus for estimating or measuring a physical area or physical volume of an object of interest in one or more images captured using an endoscope are disclosed. According to the present method, one or more structured-light images and one or more regular images captured using an imaging apparatus are received. An object of interest in the regular images is determined. Distance information associated with the object of interest with respect to the imaging apparatus is derived from the structured-light images. The physical area size or physical volume size of the object of interest is determined based on the regular images and the distance information. The imaging apparatus can be a capsule endoscope or an insertion endoscope.

25 Claims, 8 Drawing Sheets

Related U.S. Application Data which is a continuation-in-part of application No. 15/669,853, filed on Aug. 4, 2017, now Pat. No. 10,346,978.

(51) Int. Cl.
| | | |
|---|---|---|
| *G06T 7/62* | (2017.01) |
| *G06T 7/12* | (2017.01) |
| *G06T 7/00* | (2017.01) |
| *A61B 5/107* | (2006.01) |
| *A61B 1/04* | (2006.01) |

(56) References Cited

U.S. PATENT DOCUMENTS

| | | |
|---|---|---|
| 10,402,992 B2 * | 9/2019 | Wang .................... A61B 5/1076 |
| 10,531,074 B2 * | 1/2020 | Wilson ................. H04N 13/254 |
| 2010/0272318 A1 | 10/2010 | Cabiri et al. |
| 2012/0035507 A1 | 2/2012 | George et al. |
| 2017/0046833 A1 | 2/2017 | Lurie et al. |

\* cited by examiner

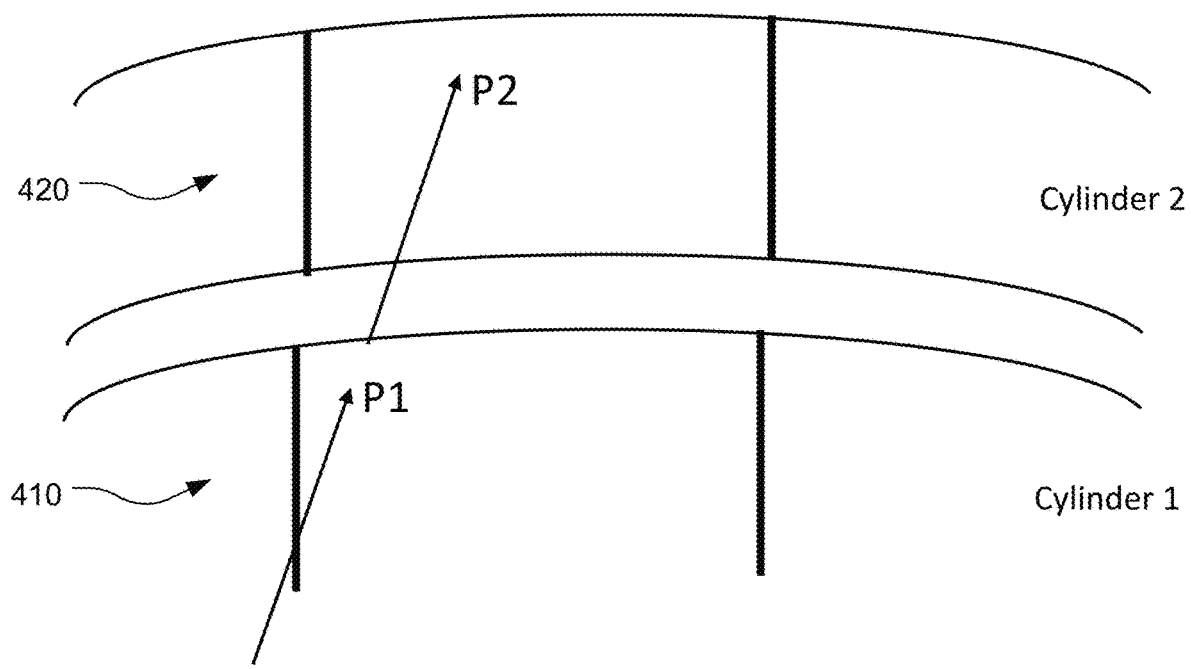
*Fig. 4A*
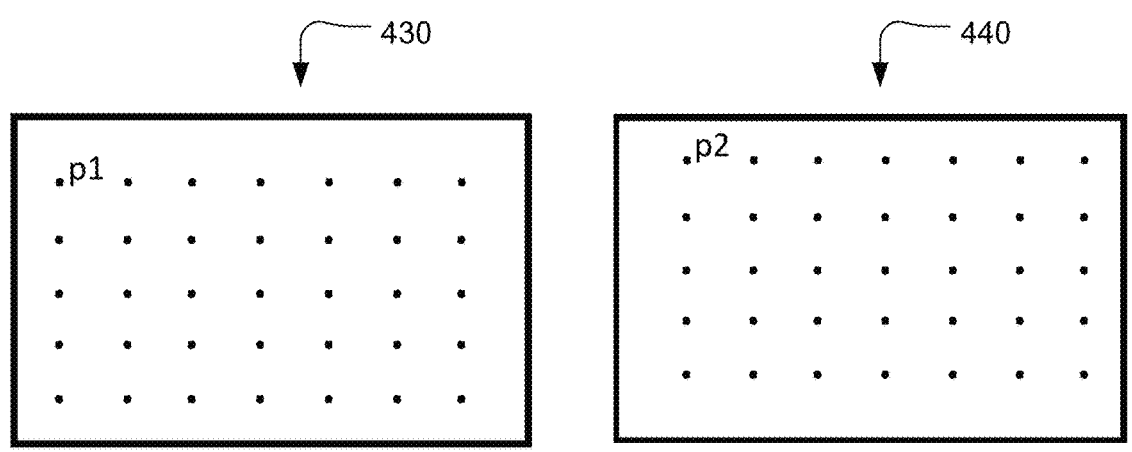
*Fig. 4B*  *Fig. 4C*

METHOD AND APPARATUS FOR ESTIMATING AREA OR VOLUME OF OBJECT OF INTEREST FROM GASTROINTESTINAL IMAGES

CROSS REFERENCE TO RELATED APPLICATIONS

The present invention is a continuation-in-part application of and claims priority to U.S. Patent Application, U.S. Ser. No. 16/416,266, filed on May 20, 2019, which is a continuation-in-part application of and claims priority to U.S. Patent Application, U.S. Ser. No. 15/669,853, filed on Aug. 4, 2017, now U.S. Pat. No. 10,346,978, issued on Jul. 9, 2019. The present invention is also related to U.S. Patent Application, U.S. Ser. No. 14/884,788, filed on Oct. 16, 2015, which is now a U.S. Patent, U.S. Pat. No. 9,936,151, issued on Apr. 3, 2018. The U.S. Patent Applications and U.S. Patent are hereby incorporated by reference in their entireties.

FIELD OF THE INVENTION

The present invention relates to the endoscope for capturing images of human gastrointestinal (GI) tract for diagnosis purpose. In particular, the endoscope is enabled to estimate physical area or physical volume of an object of interest in the GI images based on structured light images.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools.

Capsule endoscope is an alternative in vivo endoscope developed in recent years. For capsule endoscope, a camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. The capsule camera with on-board storage archives the captured images in on-board non-volatile memory. The capsule camera is retrieved upon its exiting from the human body. The images stored in the non-volatile memory of the retrieved capsule camera are then accessed through an output port on in the capsule camera.

When the endoscope is used for imaging the human GI tract, one of the primary purposes is to identify any possible anomaly. If any anomaly is found, it is further of interest to determine characteristics of the anomaly, such as the size of the anomaly. For example, the polyp size is an important clinical factor associated with surveillance interval decision making for the colonoscopy procedure. Usually, a large polyp size is associated with a higher probability of malignancy. Furthermore, for cancerous tumor, the size will affect the probability of lymphovascular invasion and metastasis, and also impact prognosis substantially. For example, in a technical paper by Warren et al., ("Comparison of One-, Two-, and Three-Dimensional Measurements of Childhood Brain Tumors", *Journal of National Cancer Institute*, pp. 141-145, Vol. 93, No. 18, Sep. 19, 2001), it shows that the tumor lymphovascular metastasis is more closely related to tumor area or volume, i.e. multiple dimensional measurement than a dimensional measurement. Similar observation has also been noted by Kikuchi et al., ("A new staging system based on tumor volume in gastric cancer', *Anticancer Research*, pp. 2933-2936, Vol. 21, No. 4B, July-August 2001).

However in the colonoscopy standard procedure, the polyp size is always measured by its longest dimension. For example, in a technical article by Chaptini et al, ("Variation in polyp size estimation among endoscopists and impact on surveillance intervals", *Gastrointestinal Endoscopy*, pp. 652-659, Volume 80, No. 4: 2014), the polyp size is determined by measuring the size of the open forceps from the printed photograph or images displayed on a display device. Similar size measuring technique has also been mentioned by Plumb et al., ("Terminal digit preference biases polyp size measurements at endoscopy, computed tomographic colonography, and histopathology", *Endoscopy*, pp. 899-908, Vol. 48, October 2016).

It is desirable to develop techniques that can easily measure or estimate the physical area or physical volume of an object of interest.

BRIEF SUMMARY OF THE INVENTION

A method for estimating a physical length, physical area or physical volume of an object of interest in a regular image captured using an endoscope is disclosed. According to this method, one or more structured-light images are received, where the structured-light images are captured using the imaging apparatus by projecting structured light onto a body lumen when the imaging apparatus is in the body lumen. One or more regular images are received, where the regular images are captured using the imaging apparatus by projecting non-structured light onto the body lumen when the imaging apparatus is inside the body lumen. The object of interest in the regular images is determined, where the object of interest corresponds to a target object on a wall of the body lumen. The distance information associated with the object of interest with respect to the imaging apparatus is derived from the structured-light images. The physical area size or physical volume size of the object of interest is determined based on the regular images and the distance information. The imaging apparatus can be a capsule endoscope or an insertion endoscope.

The steps of determining the physical area size or the physical volume size of the object of interest may comprise: determining a first direction aligned with a longest straight line from one end of the object of interest to another end of the object of interest; estimating a first physical dimension of the object of interest based on the longest straight line measured from said one or more regular images scaled by a magnification factor associated with optical configuration of an image sensor of the imaging apparatus; and estimating a second physical dimension of the object of interest based on a second measured longest length of the object of interest in a second direction scaled by the magnification factor, wherein the second direction is perpendicular to the first direction. The physical area size of the object of interest is proportional to a product of the first physical dimension of the object of interest and the second physical dimension of the object of interest.

In one embodiment, the object of interest can be determined by outlining a boundary of the object of interest by a user or an artificial intelligence process or jointly by the user and the artificial intelligence process. The step of outlining the boundary of the object of interest can be performed by the user using an input device to indicate the boundary of the object of interest in said one or more regular images displayed on a display device. If the object of interest crosses the boundary of a current regular image into one or more neighboring regular images, the current regular image and said one or more neighboring regular images are stitched prior to said determining the physical area size or the physical volume size of the object of interest. The object of interest can be outlined in the current regular image and said one or more neighboring regular images to assist stitching the current regular image and said one or more neighboring images.

The step of determining the object of interest may comprise outlining a boundary of the object of interest automatically using image processing. The physical area size or the physical volume size of the object of interest can be determined automatically by using computer executable codes executed on a computing device. The object of interest may correspond to a lesion, pedunculated polyp, sessile serrated polyp, flat lesion or an infected area by Crohn's disease.

In one embodiment, a score board can be generated for an anomaly as an indication of condition of the anomaly by using an aggregate number corresponding to an average area or percentage of one or more target objects of interest in one or more first regular images representing a section of GI (gastrointestinal) tract, where the target objects of interest correspond to one or more infected areas in the GI tract associated with the anomaly. The section of GI tract may correspond to a part of small bowel, a part of colon or both.

In one embodiment, an index number is generated for an anomaly as an indication of a disease state for the anomaly, where the index number is proportional to a sum of infected areas in said one or more regular images in a GI (gastrointestinal) section divided by a sum of total image areas in said one or more regular images in the GI section.

In one embodiment, the object of interest corresponds to an anomaly and the physical volume size of the object of interest is derived based on a 3D mathematical model for the anomaly and measured 1D or 2D size information for the object of interest, where the 3D mathematical model is used to predict depth or volume of the anomaly underneath a mucosal surface. The 3D mathematical model may correspond to an ellipsoid, ovoid, sphere or disc.

In one embodiment, the physical area size or the physical volume size of the object of interest is derived based on the distance information that is derived at a set of point locations by projecting the structured light onto the body lumen. A triangle mesh is generated to cover a topographic surface of the object of interest, where the triangle mesh consists of a set of triangles generated using the set of point locations. In one embodiment, an outline identifying the object of interest is projected onto the triangle mesh and projected area of a target set of triangles within the outline projected is determined as the physical area size of the object of interest. In another embodiment, a vector sum of target triangles of the target set of triangles is calculated, where each vector area associated with each target triangle corresponds to a product of area and normal vector of each target triangle. In still yet another embodiment, a 3D shape model is assumed for the object of interest and the physical volume size of the object of interest is estimated based on a measured 1D or 2D size information for the object of interest.

BRIEF DESCRIPTION OF THE DRAWINGS

FIG. 4A illustrates an example of a uniform background on the surface of a cylinder at two difference distances (Z1 and Z2) from the camera.

FIG. 4B illustrates an example of a captured image by projecting N dots at distance Z1, where the upper left dot is labelled as q1.

FIG. 4C illustrates an example of a captured image by projecting N dots at distance Z2, where the upper left dot is labelled as q2.

FIG. 4D illustrates an example of some epipolar lines in the upper-left portion derived from the captured images in FIG. 4B and FIG. 4C.

FIG. 4E illustrates an example in real scenario, when a target light ray intersects with the tissue surface, the projection of the intersection point falls into this ray's epipolar line as a dot.

DETAILED DESCRIPTION OF THE INVENTION

Figure 1A:
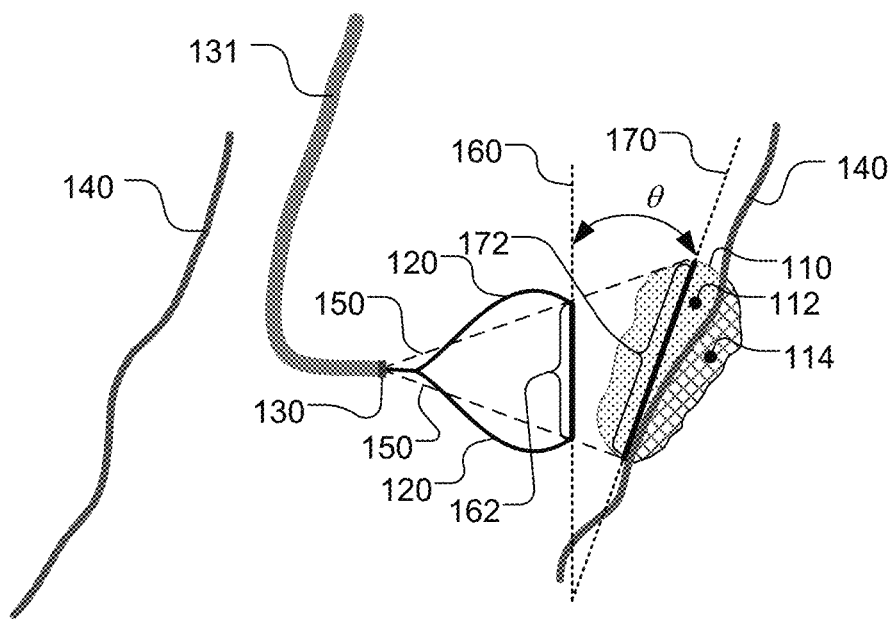
FIG. 1A illustrates an example of measuring the longest dimension of a tumor using a forceps, where an angle exists between the image plane and the object plane.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Endoscopes are normally inserted into the human body through a natural opening such as the mouth or anus. Therefore, endoscopes are preferred to be small sizes so as to be minimally invasive. As mentioned before, endoscopes can be used for diagnosis of human gastrointestinal (GI) tract. The captured image sequence can be viewed to identify any possible anomaly. For example, polyp is an anomaly that a doctor often looks for during the colonoscopy procedure. The polyp size is an important clinical factor associated with surveillance interval decision making for the colonoscopy procedure. Moreover Crohn's disease is more prevalent in the western world. The diagnosis and follow-up of the disease state include endoscope direct visualization of mucosa surface in the upper and lower gastrointestinal tracts. However, the gastroenterologist has to insert and maneuver the endoscope through the convoluted human intestine laboriously in order to observe the mucosa surface and obtain a subject impression of the disease condition, such as how prevalent the inflammation condition is inside the GI tract. Alternatively, an ingestible capsule endoscope can be used to examine the GI tract.

If any anomaly is found, it is of interest to identify the characteristics of the anomaly. There exists a significant unmet need to assess area or volume of an object of interest in the GI tract. This assessment is confounded by a few issues in the current state of the art endoscope technology. The measurement currently is always one dimensional, which uses a device of known size (e.g. a forcipes) to align and to get close to the polyp. The forcipes is aligned with its longest dimension to estimate the polyp size by comparison with the forcipes of known size. However the endoscope comprises a flexible cable and when inserted inside a tortuous intestine, the precise maneuver could not be done with ease and precision. Even if alignment with the longest dimension is successful, usually there will be an angle between the longest dimension of the tumor and the forcipes. For an ingestible capsule, the maneuver is out of question.

Moreover, the lesion might not be on the same plane. For example, in the case of a flat lesion in colon or the inflammation in the case of Crohn's disease, this makes the accurate measurement untenable.

Figure 1B:
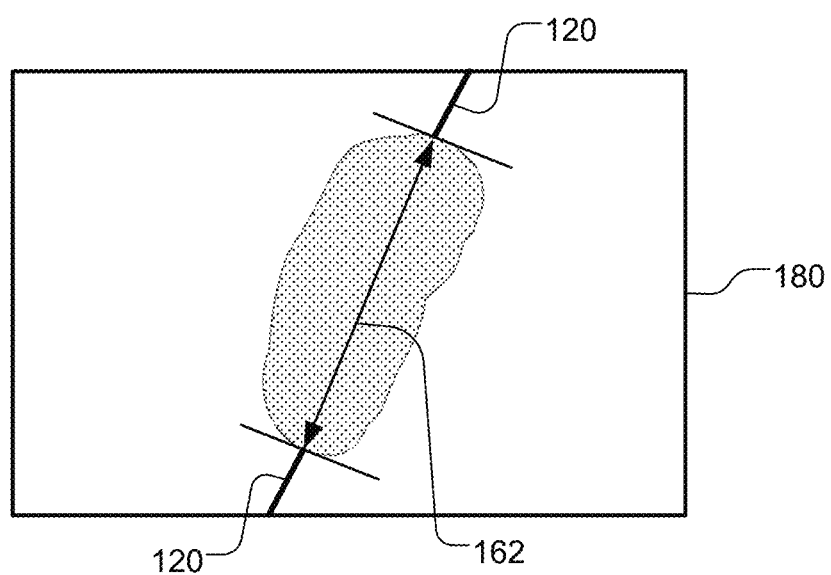
FIG. 1B illustrates an example of measuring the longest dimension of an object of interest using a forceps to align with the longest dimension of the tumor as seen from an endoscope image.

FIG. 1A illustrates a cross section view for an example of measuring the longest dimension of a tumor 110 using a forcipes 120. The distal end 130 of the endoscope snake cable 131 is inserted into the GI tract, where lines 140 indicate the mucosal surface. Part of the tumor (112) is above the mucosal surface 140 and part of the tumor (114) is underneath the mucosal surface. Furthermore, the distal end 130 has a camera and LED light (not explicitly shown) to capture images. Also, there is an opening at the distal end to allow forcipes 120 to extend out for size measurement. The forcipes is aligned with the longest dimension of the tumor to estimate the tumor size. In FIG. 1A, dash lines 150 indicate the alignment of the tips of forcipes 120 with the longest dimension of the tumor as seen from the endoscope image 180 in FIG. 1B. However, the image plane 160 and the object of inter plane 170 may not be aligned. In FIG. 1A, there is an angle θ between the image plane and the object of interest plane. The measured longest dimension 162 is shorter than the physical longest dimension 172 as shown in FIG. 1A.

In order to overcome the deficiencies in the conventional size measurement of an object of interest, an invention of the present invention discloses an endoscope system that allows a user to easily measure the area or volume of an anomaly. According to the present invention, an endoscope, tethered or untethered such as an ingestible capsule, with distance measurement capability is disclosed to overcome the above issues existing in the state of the art in diagnosis.

In PCT Patent Application, Serial No. PCT/US17/15668, filed on Jan. 30, 2017, a method to measure 1D size of an object of interest from the captured image and distance information has been disclosed. The method according to PCT/US17/15668 relieves the needs for the laborious procedure requiring a forcipes in the conventional approach. According to PCT/US17/15668, the true size of an object of interest can be estimated from the measured size in the captured image and a determined object distance. In an endoscope, the focal length is known by design. If the distance (also named as object distance in this disclosure) between an object and the camera can be determined, the dimensions of an object can be determined simply using geometry.

Figure 2:
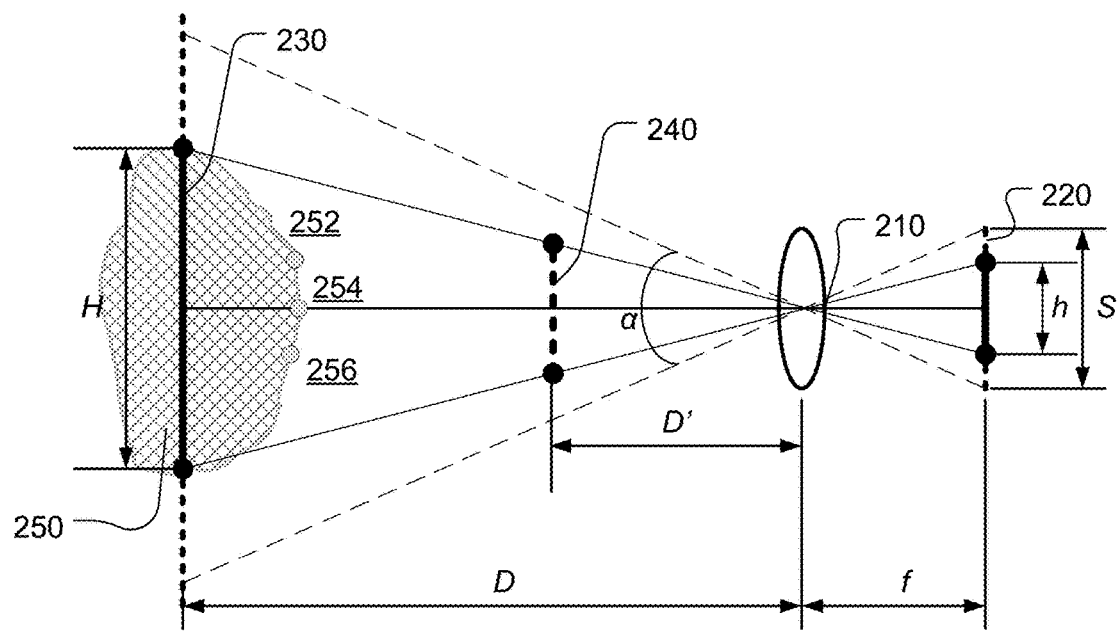
FIG. 2 illustrates a simplified example of object dimension determination based on object-camera distance.

FIG. 2 illustrates a simplified example of object dimension determination based on object-camera distance. In a camera system, the image sensor is placed at the focal plane 220 behind the lens 210. The camera can capture a scene within the field of view extending an angle a. The focal length f is the distance between the lens and the image sensor. The focal length often is fixed for endoscopic applications and is known by design. However, when a capsule endoscope travels through the GI tract, the object distance D varies depending on the location of the capsule endoscope and its relative angles with respect to the GI wall being imaged. If the distance D is known, the dimension of an object can be determined from the captured image by measuring the size of the object image in the image. For example, if a flat object 230 with height H is at distance D from the camera, the object image height H can be derived from the object image height h in the image according to:

$$H = \left(\frac{D}{f}\right)h. \quad (1)$$

In the above equation, h is measured from the image, the focal length f is known by design, and the distance D is determined by a selected distance measuring means as mentioned above. Accordingly, if the distance can be determined, the object dimensions can be derived. For an actual object, a single object-camera distance is not adequate to estimate the object size in area or volume accurately. Therefore, it is desirable to determine object-camera distance at multiple locations. In FIG. 2, object 250 corresponds to a cross section of a 3D object. Locations 252, 254 and 256 corresponds to three locations on the object surface. With object-camera distances (z-axis) known at multiple locations (x and y axis), a 3D model of the object surface can be established and the surface are of the object can be estimated accordingly. For the locations without the object-camera distance, the distance information can be interpolated from known object-camera distances.

According to embodiments of the present invention, the object size in the image is measured in physical dimension. The image is captured digitally and the size measurement may be more convenient in terms of the number of pixels. Since the physical dimension of image sensor surface and the optical footprint are known. Also, the number of pixels is known (e.g. 320×240). Therefore, the object image size in the image can be measured in a number of pixels and converted physical object image size in the image. For convenience, the ratio D/f is referred as magnification factor. With the object-camera distance known at a location (i.e., a 3D location), a small area around the location on the surface can be assigned with this magnification factor for area estimation. Furthermore, if a 3D model is derived for the object surface, the surface area can be calculated using any known area calculation technique. For example, a net of polygons for the surface is determined and the area of the surface can be calculated as a sum of areas of individual polygons.

As shown above, the object image size in the image depends on the actual object size and its distance from the camera. A smaller object at a closer distance may appear to have the same size in the image as a larger object at a farther distance. For example, the object 240, which is smaller but closer than object 230, appears to have the same height as object 230 in the image. Therefore, the distance is crucial information for determining the object size. Accordingly, the distance measuring means disclosed above enables object size determination based on the images captured using an endoscope.

In U.S. Patent, U.S. Pat. No. 9,936,151, issued to the same assignee as the present application, a method of capturing one or more structured-light images and associated regular images are disclosed. The method captures a structured-light image and an associated regular image with a reduced frame interval in between so that the amount of any movement between the two images is reduced. Accordingly, the depth or distance information derived from the structured-light image according to U.S. Patent, U.S. Pat. No. 9,936,151 is more correlated with the associated regular image. However, the present invention is not limited to the depth/distance derivation based on U.S. Pat. No. 9,936,151. The present invention may use any depth/distance derivation method based on the structured-light images. An example of object-camera distance derivation is described as follows.

Figure 3A:
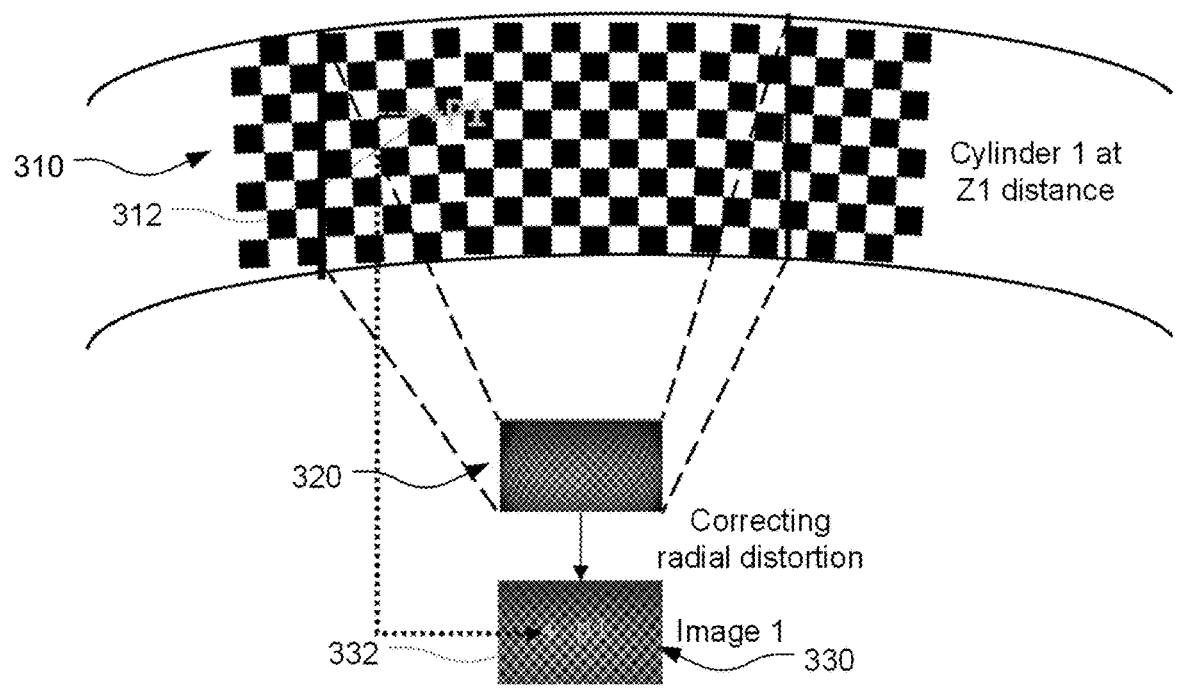
FIG. 3A illustrates an example of camera geometry correction using a checkerboard pattern on a cylinder surface at distance Z1 and the captured image is corrected or de-warped to compensate the geometry distortion.

The system can use N light beams to detect the object-camera distance at N locations. However, before the system can detect the distance, some calibrations have to be performed for the camera system and the light beam projector. In order to characterize the camera geometry, some known pictures can be used as the target. For example, a picture with checkerboard patterns can be used as the target. In order to imitate the shape of the GI tract, a checkerboard pattern on a surface of a cylinder is used as the target picture. The camera geometry calibration is performed in a controlled environment. As shown in FIG. 3A, the checkerboard pattern 310 on a cylinder surface at distance Z1 is used as the target test image. Image 320 corresponds to the image captured using the camera. Due to the close distance in the GI environment and other various reasons, the captured image is subject to various distortion, in particularly the radial distortion. Therefore, the captured image needs to be corrected. Image 330 corresponds to the corrected/dewarped image. Each corner pixel p(x1,y1) on the corrected/dewarped image corresponds to a 3D location P(X1,Y1,Z1) on cylinder 1.

Figure 3B:
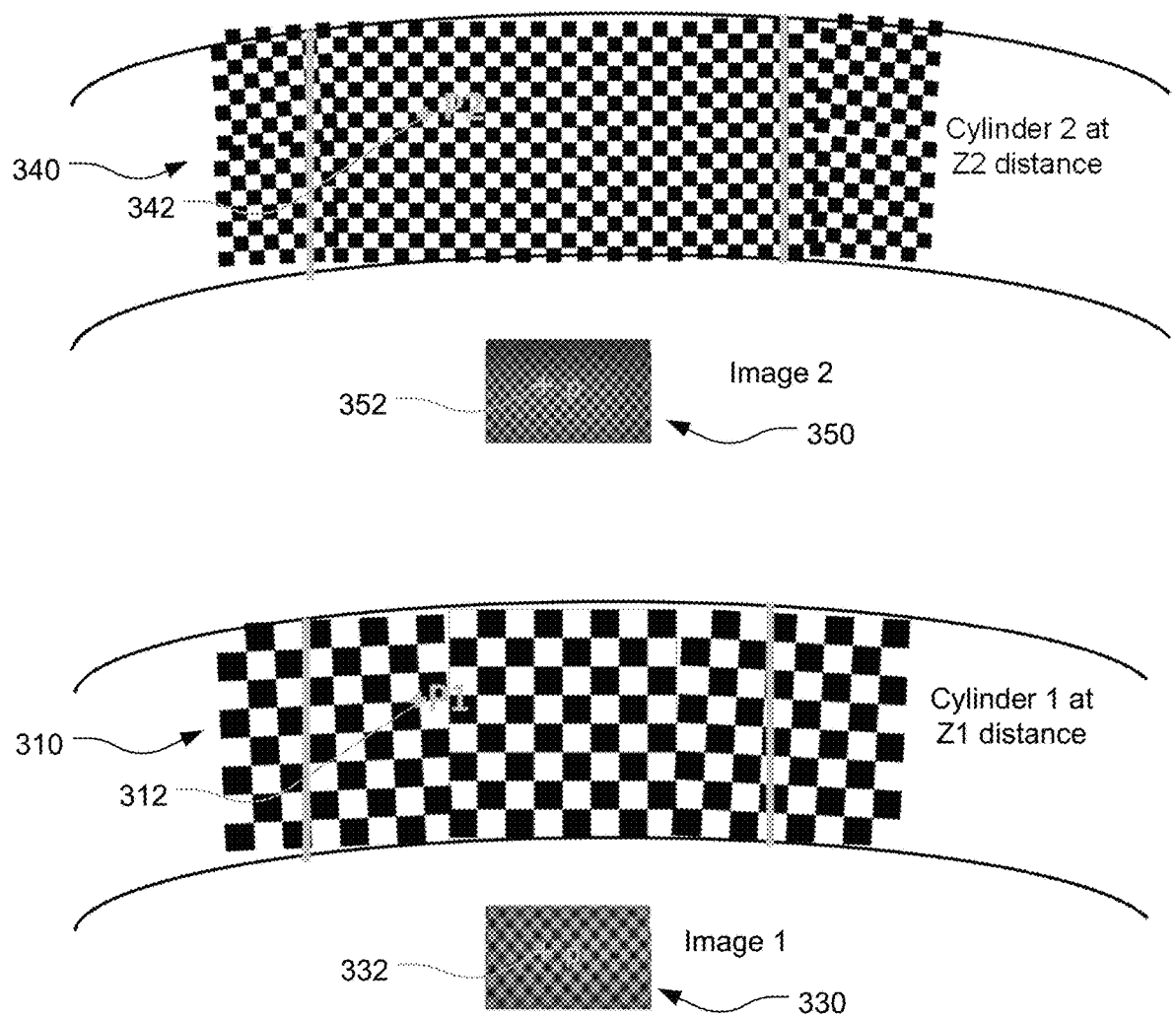
FIG. 3B illustrates an example of camera optic characterization using a checkerboard pattern on a cylinder surface at two distances Z1 and Z2 to derive camera rays.

Since we know the cylinder distance, size and location of each square of the checkerboard, we can easily calculate the 3D location of each corner at checkerboard. In other words, given a pixel p1 (332) on image 1, we know its 3D location P1 (312) on cylinder 1. For any other pixel inside corners, we can use bilinear interpolation to recover its 3D location. In order to establish a camera geometry model, an embodiment according to the present invention captures two pictures at two different distances (e.g. Z1 and Z2). For image 2, the checkerboard pattern on the cylinder 340 is displayed at distance Z2 as shown FIG. 3B. An image is captured using the camera and the captured image is corrected to image 350. The 3D location P2 342 of the checkerboard at distance Z2 corresponds to the 3D location P1 312 on the checkerboard at distance Z1. Now for each image pixel (e.g. same pixel p (332) in image 1 (330) and pixel p (352) in image 2 (350)) in the corrected image plane, we know a pair of 3D points, {P1, P2}. Each pair of two 3D points defines a camera ray for the corresponding image pixel p. This will replace the model that uses camera optical center of projection to form a camera ray. Based on our experiments, the capsule system cannot be properly modeled as a perfect pinhole camera. While the checkerboard pattern is used as an example of test image, other test images with known patterns may also be used. For example, a group of "dots" with size, color or line type variations at known locations can be used so that individual "cross marks" can be discerned.

The camera system, particularly the camera optical system, for each capsule device is subject to manufacturing variations. Therefore, the camera geometry has to be calibrated individually for each capsule device before the capsule camera placed for use. The camera calibration data can be stored in a non-volatile memory such as NVRAM (non-volatile random access memory).

After camera geometry is calibrated, the system calibrates the projector geometry by projecting N light beams to a uniform background (e.g. white/gray background) at two different distances (e.g. Z1 and Z2 corresponding to the minimum and maximum intended object distance). For example, FIG. 4A illustrates an example of a uniform background (410 and 420) on the surface of a cylinder at two difference distances (Z1 and Z2) from the camera. For projecting the light beams, a light source (e.g. a laser or an LED (light emitting diode) can be used to project multiple light beams through an optical system to the field of view.

For example, a light beam is projected to location P1 in the background at distance Z1 and location P2 in the background at distance Z2. Projection of P1 and P2 on corrected image plane will be p1 and p2 respectively. Correction based on the camera geometry can be applied to the epipolar lines to become straight. Using the step similar to the camera geometry calibration, the pair P1 and P2 forms a projector ray.

FIG. 4B corresponds to a captured image by projecting N dots at distance Z1, where the upper left dot is labelled as q1. FIG. 4C corresponds to a captured image by projecting N dots at distance Z2, where the upper left dot is labelled as p2. Each corresponding dot pair forms an epipolar line. Some epipolar lines in the upper-left portion are shown in FIG. 4D. In practice, the projection system for each capsule camera is subject to manufacturing variation. The projector geometry calibration is performed individually. The projector geometry calibration data can be stored inside the capsule camera using non-volatile memory such as NVRAM.

In real scenario, when the same light ray intersects with the tissue surface, the projection of the intersection point will fall into this ray's epipolar line as a dot (e.g. position q in FIG. 4E). For each dot of the projected beams, we need to detect and identify the dot. Since we know the projector ray of this epipolar line as well as the camera ray for the pixel at the center of the dot, we can use standard triangulation to compute the 3D location at the intersection of above two rays. One such method is called mid-point method. According to this method, we first define L1 as the projector ray and L2 as the camera ray. Furthermore, we define d(P, L) as the Euclidean distance between ray L and a 3D point P. We will find the best P which minimizes $d(P,L1)^2+d(P,L2)^2$. By this means, we can recover the 3D position for all N dots. (another maybe unnecessary clarification: It is necessary to find the correct correspondence between the projected beams and the spots on the image. This is done with an assignment algorithm. Some epipolar lines cross, sometimes dots are missing and sometimes there is extra stray light. The assignment algorithm attempts to account for all these possibilities by choosing the solution that best matches typical geometry found in the GI tract).

In order to reduce the required computation, an embodiment of the present invention builds a lookup table after the epipolar lines are calculated. We sample M points along each epipolar line and precompute the 3D position for each sampled point using above triangulation. For example, if an epipolar line corresponds to an object distance between 0 cm to 5 cm, we can divide the range into target distances at 0.1 cm increment (i.e., 0, 0.1, 0.2, . . . , 4.8, 4.9, 5.0 cm) and precompute the 3D points for target distances within the range. If a dot falls between two sampled points, we use linear interpolation to compute the 3D position.

An example of interpolation is illustrates as follows. First, the weight w is computed according to:

$w=|p-p1|/|p2-p1|.$

The corresponding 3D position Z will be computed according to:

$Z=Z1+w*(Z2-Z1)$

In the above, one example of distance derivation is illustrated. However, the present invention is not limited to this particular distance derivation method.

In one embodiment of the present invention, the boundary of the lesion is outlined first. The method based on this embodiment identifies the first longest dimension and measure its length according to the information of distance and magnification of the imager. Since the endoscope image plane may not be aligned with the lesion plane well, the distance information from a multiple point in the field of view may be required.

For the embodiment above, the present method may further provide a tool to find the second longest dimension in the direction perpendicular to the direction of the first longest dimension. The 2D measurement of the lesion can be expressed as the product of the first longest dimension and the second longest dimension that are derived above with the 1D dimension information as a by-product in the process.

In another embodiment, a method according to this embodiment provides a tool to measure the real area accurately by using a variety of area measuring methods, such as using grids.

In yet another embodiment, a method according to this embodiment allows a user (e.g. a doctor or a medical professional), an algorithm implemented in computer/software codes or both to outline the lesion in the image. For example, a medical professional may draw the outline on a touch screen that displays the GI image being examined. A computer may run a program trained by deep learning to automatically draw the outline of a lesion. In yet another example, a doctor may point to a location on the lesion in the image and the computer with AI (artificial intelligence) may take over to finish the outlining automatically. The use of deep learning or artificial intelligence to perform various image processing tasks (e.g. pattern recognition) is well known in the field. The details are not repeated here.

For the GI image, each image typically covers limited a field of view. Therefore, it may occur that a tumor, especially the Crohn's disease inflammation, may cross the image boundaries. The whole tumor may spread over a number of images. According to one embodiment of the present invention, image stitching is performed first and area or volume measurement is performed based on the stitched image.

While fully automated area or volume measure of an object of interest is feasible, the system may perform faster or more reliably with some degree of human assistance. For example, the stitching across multiple images may be assisted by the outlining boundaries of the lesion, which can be designated as a "feature". The method then estimates the size or volume of the "feature".

During the process of estimating the area or volume based on stitched image, a score board can be kept by using an aggregate number. The aggregate number may correspond to an average area or percentage of infected area per image. The aggregate number may also be calculated for each area (e.g. aggregated areas of all images) calculated through a section of the GI tract, such as the small bowel, ileum, colon, etc. Therefore, the disease state can be indicated by an index number proportional to the sum of infected areas in the total images in a GI section divided by the sum of image areas of images in the section.

The 3D size (i.e., the volume) may be calculated based on a mathematical model for each type of lesion, pedunculated polyp, sessile serrated polyp, flat lesion, etc. This model may predict the depth of the lesion under the surface, which is useful in the assessment of probability of metastasis.

Figure 5:
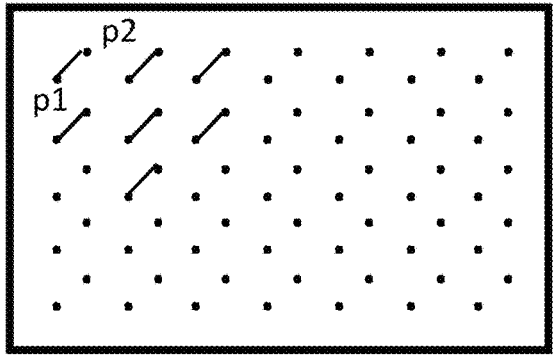
FIG. 5 illustrates an example of a triangle mesh formed from the structured light points.
Figure 5:
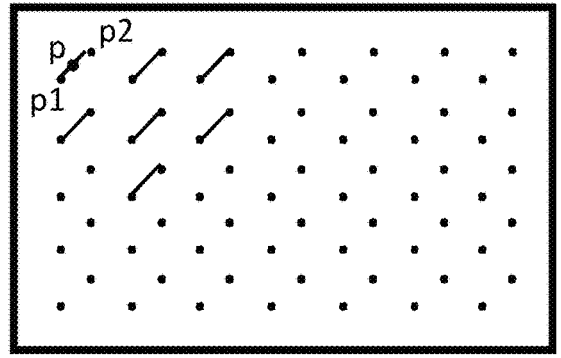
Figure 5:
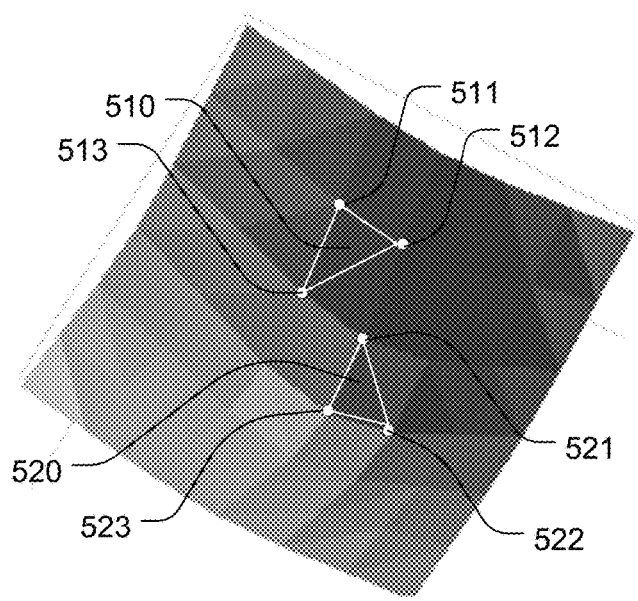

According to another embodiment of the present invention, structured light is used to estimate the 3D size. For example, a number of point locations in 3D can be obtained by using structured light, where the structured light ray intersects with the walls of the lumen. An approximate continuous depth map can be formed by connecting the known points together in a triangle mesh. FIG. 5 illustrates an example of a triangle mesh formed from the structured light points. For example, triangle 510 is formed from three structured light points 511, 512 and 513. Triangle 520 is formed from three structured light points 521, 522 and 523. The triangle mesh is formed similar to Delaunay triangulation. Each of the triangles formed is a flat plane surface intersecting with the three points that comprise the triangles vertices. The plane can be found by interpolating the three depth values.

The normal intensity/color image may show a feature, which can be encircled by a user or a software tool. The algorithm below illustrates an example used to calculate the silhouette area or shadow area of this feature.

Figure 6:
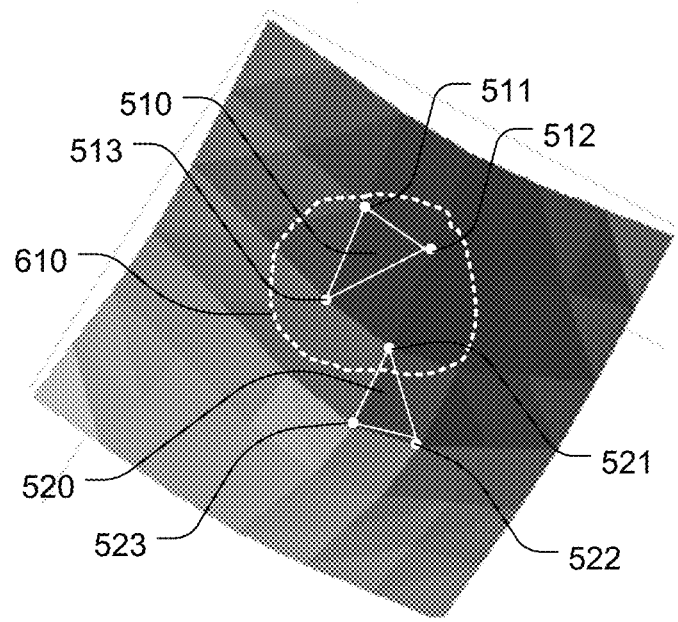
FIG. 6 illustrates a free hand loop indicating a feature can be projected onto the triangle mesh.

A free hand loop 6610 to indicate a feature can be projected onto the triangle mesh as shown in FIG. 6. The area component from each triangle can be found by simply determining the 2D intersection area of the triangle and the projected free hand loop.

Figure 7A:
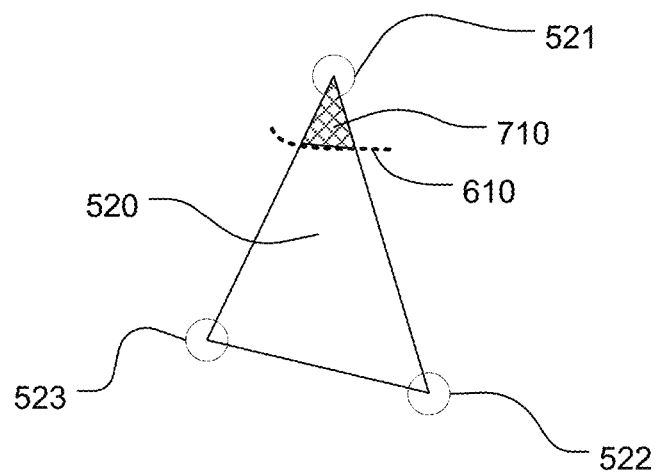
FIG. 7A illustrates an example that a portion of a triangle inside the free hand loop is indicated by the hatch-line filled area.

A triangle (i.e., 520) across the free hand loop as shown in FIG. 7A contributes partially to the area size estimation. For triangle 520, only the portion (i.e., 710) inside the free hand loop 610 is counted for area calculation. The portion inside the free hand loop 610 is indicated by the hatch-line filled area 710 in FIG. 7A. A triangle (e.g. triangle 510) may also be entirely in the interior of the free hand loop. In this case, the triangle contributes the entire area to the area size calculation. On the other hand, a triangle may be on the exterior of the free hand loop and does not contribute to the area size at all. In practice we normally subdivide mesh to denser and smoother mesh. It's easy to compute the interior area of the free hand drew contour based on more detailed mesh.

Figure 7B:
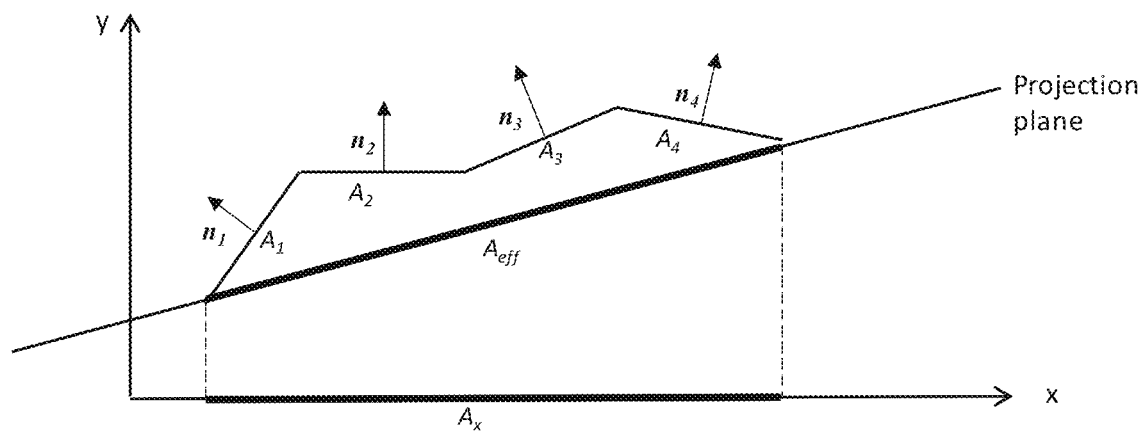
FIG. 7B illustrates an example of computing surface area or cross section area according to an embodiment of the present invention.

We can compute surface area or cross section area as shown in FIG. 7B. $A_i$ is surface area, $n_i$ is surface normal, $A_{eff}$ is the cross section area by projecting the mesh to a plane whose normal $n=\Sigma(n_i)/\|(n_i)\|$ A projected (cross section) area $A_{eff}$ of the tumor can be defined as:

$$A_{eff} = \Sigma_i^K A_i * (\hat{n}_i \cdot n)$$

In yet another implementation, a surface area $A_{surface}$ can be determined from:

$$A_{surface} = \sum_i^K A_i$$

The area derived as above is a better measurement of the size of a tumor than the simply linear (i.e., 1D) dimension for indicating disease state.

In yet another embodiment, the feature is assumed to fit a shape (e.g. ellipsoid, ovoid, sphere, disc or more complicate 3D shapes.). Therefore, the volume for the feature can be estimate from the shape assumption and parameter(s) associated with the shape using the 3D model of the object surface.

Figure 8:
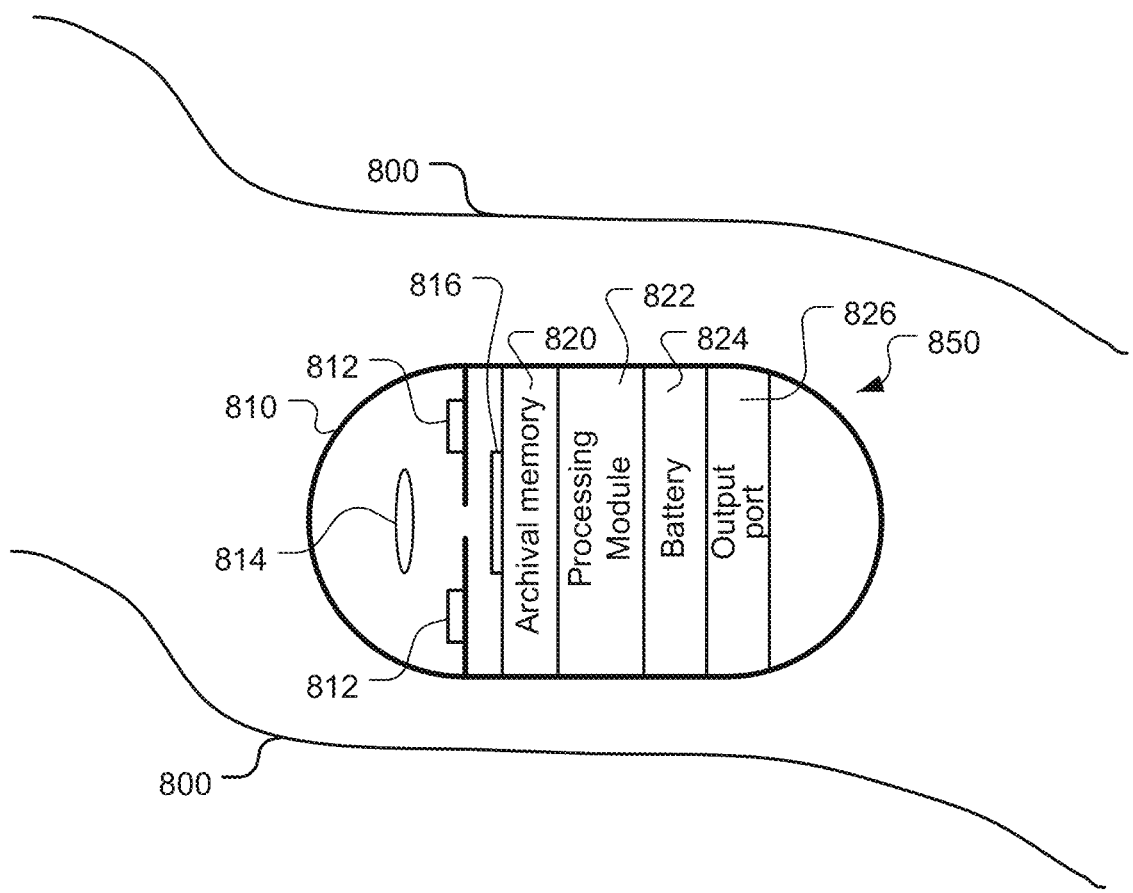
FIG. 8 illustrates an exemplary capsule system with on-board storage.

FIG. 8 illustrates an exemplary capsule system with on-board storage. The capsule device 850 includes illuminating system 812 and a camera that includes optical system 815 and image sensor 816. A semiconductor nonvolatile archival memory 820 may be provided to allow the images to be stored and later retrieved at a docking station outside the body, after the capsule is recovered. Capsule device 850 includes battery power supply 825 and an output port 826. Capsule device 850 may be propelled through the gastrointestinal (GI) tract by peristalsis.

Illuminating system 812 may be implemented by LEDs. In FIG. 8, the LEDs are located adjacent to the camera's aperture, although other configurations are possible. The illuminating light source may also be provided, for example, behind the aperture. Other illuminating light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 815, which may include multiple refractive, diffractive, or reflective lens elements, provides an image of the lumen walls (800) on image sensor 816. Image sensor 816 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 816 are preferably converted into digital form to allow processing in digital form. Such conversion may be accomplished using an analog-to-digital (A/D) converter, which may be provided inside the sensor (as in the current case), or in another portion inside capsule housing 810. The A/D unit may be provided between image sensor 16 and the rest of the system. LEDs in illuminating system 812 are synchronized with the operations of image sensor 816. Processing module 822 may be used to provide processing required for the system such as image processing and video compression. The processing module may also provide needed system control such as to control the LEDs during image capture operation. The processing module may also be responsible for other functions such as managing image capture and coordinating image retrieval.

After the capsule camera traveled through the GI tract and exits from the body, the capsule camera is retrieved and the images stored in the archival memory are read out through the output port. The received images are usually transferred to a base station for processing and for a diagnostician to examine. The accuracy as well as efficiency of diagnostics is most important. A diagnostician is expected to examine the images and correctly identify any anomaly. While the on-board archival memory is used for storing the captured images, a wireless transmitter can be used to send to captured images to a receiver located out the human body.

In order to capture structured light images, the capsule camera needs a projection system (not shown in FIG. 8) to project the light beams with a known pattern. The projection system comprises a projection light source (e.g. a laser or LED) and an optical system. The same image sensor 816 can be used to capture the structured light image. The processing module 822 or a separate processor can be used to perform the computations required to derive the distance information at various beam locations. When a table is used to store pre-computed 3D points at various target distances, a storage device (e.g. NVRAM (non-volatile random access memory) or ROM (read-only memory)) can be used. The archival memory may also be used to store the table.

Figure 9:
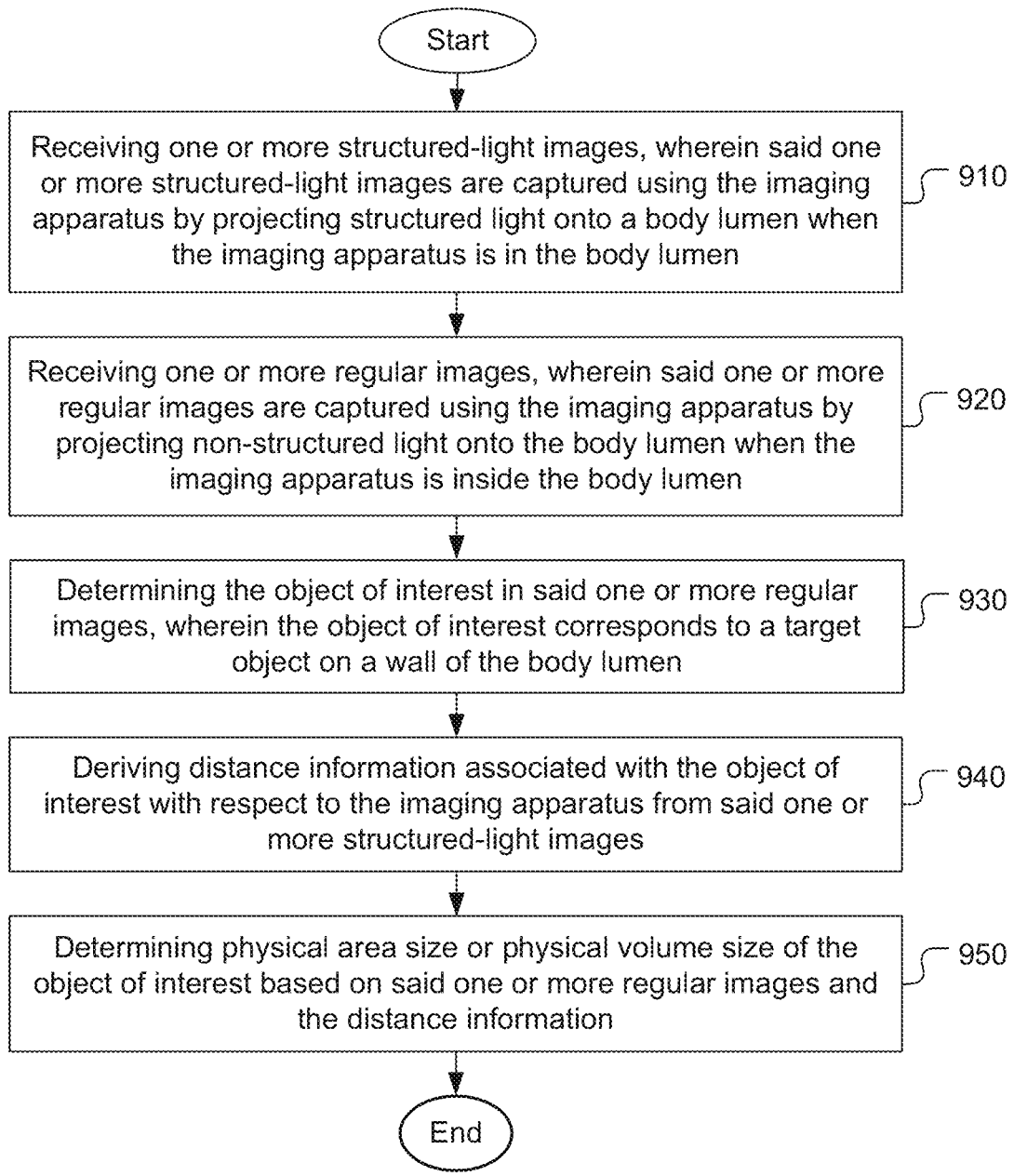
FIG. 9 illustrates an exemplary flowchart for estimating or measuring a physical length, physical area or physical volume of an object of interest in one or more images captured using an endoscope according to an embodiment of the present invention.

FIG. 9 illustrates an exemplary flowchart for estimating or measuring a physical length, physical area or physical volume of an object of interest in one or more images captured using an endoscope according to an embodiment of the present invention. The steps shown in the flowchart, as well as other following flowcharts in this disclosure, may be implemented as program codes executable on one or more processors (e.g., one or more CPUs) at the encoder side and/or the decoder side. The steps shown in the flowchart may also be implemented based hardware such as one or more electronic devices or processors arranged to perform the steps in the flowchart. One or more structured-light images are received in step 910, wherein said one or more structured-light images are captured using the imaging apparatus by projecting structured light onto a body lumen when the imaging apparatus is in the body lumen. Said one or more regular images are received in step 920, wherein said one or more regular images are captured using the imaging apparatus by projecting non-structured light onto the body lumen when the imaging apparatus is inside the body lumen. The object of interest in said one or more regular images are determined in step 930, wherein the object of interest corresponds to a target object on a wall of the body lumen. Distance information associated with the object of interest with respect to the imaging apparatus is derived from said one or more structured-light images in step 940. Physical area size or physical volume size of the object of interest is determined based on said one or more regular images and the distance information in step 950. The imaging apparatus can be a capsule endoscope or an insertion endoscope.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of estimating or measuring a physical area or physical volume of an object of interest in one or more regular images captured using an imaging apparatus, the method comprising:
   receiving one or more structured-light images, wherein said one or more structured-light images are captured using the imaging apparatus by projecting structured light onto a body lumen when the imaging apparatus is in the body lumen;
   receiving said one or more regular images, wherein said one or more regular images are captured using the imaging apparatus by projecting non-structured light onto the body lumen when the imaging apparatus is inside the body lumen;
   determining the object of interest in said one or more regular images, wherein the object of interest corresponds to a target object on a wall of the body lumen;
   deriving distance information associated with the object of interest with respect to the imaging apparatus from said one or more structured-light images; and
   determining physical area size or physical volume size of the object of interest based on said one or more regular images and the distance information.

2. The method of claim 1 said determining the physical area size or the physical volume size of the object of interest comprises:
   determining a first direction aligned with a longest straight line from one end of the object of interest to another end of the object of interest;
   estimating a first physical dimension of the object of interest based on the longest straight line measured from said one or more regular images scaled by a magnification factor associated with optical configuration of an image sensor of the imaging apparatus; and
   estimating a second physical dimension of the object of interest based on a second measured longest length of the object of interest in a second direction scaled by the magnification factor, wherein the second direction is perpendicular to the first direction; and
   wherein the physical area size of the object of interest is proportional to a product of the first physical dimension of the object of interest and the second physical dimension of the object of interest.

3. The method of claim 1, wherein said determining the object of interest comprising outlining a boundary of the object of interest by a user or an artificial intelligence process or jointly by the user and the artificial intelligence process.

4. The method of claim 3, wherein said outlining the boundary of the object of interest is performed by the user using an input device to indicate the boundary of the object of interest in said one or more regular images displayed on a display device.

5. The method of claim 3, wherein if the object of interest crosses the boundary of a current regular image into one or more neighboring regular images, the current regular image and said one or more neighboring regular images are stitched prior to said determining the physical area size or the physical volume size of the object of interest.

6. The method of claim 5, wherein the object of interest is outlined in the current regular image and said one or more neighboring regular images to assist stitching the current regular image and said one or more neighboring images.

7. The method of claim 1, wherein said determining the object of interest comprises outlining a boundary of the object of interest automatically using image processing.

8. The method of claim 1, wherein said determining the physical area size or the physical volume size of the object of interest is performed automatically using computer executable codes executed on a computing device.

9. The method of claim 1, wherein the object of interest corresponds to a lesion, pedunculated polyp, sessile serrated polyp, flat lesion or an infected area by Crohn's disease.

10. The method of claim 1, wherein a score board is generated for an anomaly as an indication of condition of the anomaly by using an aggregate number corresponding to an average area or percentage of one or more target objects of interest in one or more first regular images representing a section of GI (gastrointestinal) tract, and wherein said one or more target objects of interest correspond to one or more infected areas in the GI tract associated with the anomaly.

11. The method of claim 10, wherein the section of GI tract corresponds to a part of small bowel, a part of colon or both.

12. The method of claim 1, wherein an index number is generated for an anomaly as an indication of a disease state for the anomaly, and wherein the index number is proportional to a sum of infected areas in said one or more regular images in a GI (gastrointestinal) section divided by a sum of total image areas in said one or more regular images in the GI section.

13. The method of claim 1, wherein the object of interest corresponds to an anomaly and the physical volume size of the object of interest is derived based on a 3D mathematical model for the anomaly and measured 1D or 2D size information for the object of interest, and wherein the 3D mathematical model is used to predict depth or volume of the anomaly underneath a mucosal surface.

14. The method of claim 13, wherein the 3D mathematical model corresponds to an ellipsoid, ovoid, sphere or disc.

15. The method of claim 1, wherein the physical area size or the physical volume size of the object of interest is derived based on the distance information, and wherein the distance information is derived at a set of point locations by projecting the structured light onto the body lumen.

16. The method of claim 15, wherein a triangle mesh is generated to cover a topographic surface of the object of interest, and wherein the triangle mesh consists of a set of triangles generated using the set of point locations.

17. The method of claim 16, wherein an outline identifying the object of interest is projected onto the triangle mesh and projected area of a target set of triangles within the outline projected is determined as the physical area size of the object of interest.

18. The method of claim 17, wherein a vector sum of target triangles of the target set of triangles is calculated, and wherein each vector area associated with each target triangle corresponds to a product of area and normal vector of each target triangle.

19. The method of claim 16, wherein a 3D shape model is assumed for the object of interest and the physical volume size of the object of interest is estimated based on a measured 1D or 2D size information for the object of interest.

20. The method of claim 1, wherein said determining the object of interest in said one or more regular images comprises indicating the object of interest by a user via a computer input device or by executing program codes on a computer.

21. The method of claim 20, wherein said indicating the object of interest comprises generating an outline around the object of interest or changing a color or shade of the object of interest.

22. The method of claim 21, wherein the program codes include routines to utilize deep learning or artificial intelligence to automatically generate the outline around the object of interest.

23. The method of claim 1, wherein the imaging apparatus corresponds to a capsule endoscope.

24. The method of claim 1, wherein the imaging apparatus corresponds to an insertion endoscope.

25. An apparatus for estimating or measuring a physical area or physical volume of an object of interest in one or more images captured using an imaging apparatus, the apparatus comprising one or more electronic circuits or processors arranged to:
   receive one or more structured-light images, wherein said one or more structured-light images are captured using the imaging apparatus by projecting structured light onto a body lumen when the imaging apparatus is in the body lumen;
   receive one or more regular images, wherein said one or more regular images are captured using the imaging apparatus by projecting non-structured light onto the body lumen when the imaging apparatus is inside the body lumen;
   determine the object of interest in said one or more regular images, wherein the object of interest corresponds to a target object on a wall of the body lumen;
   derive distance information associated with the object of interest with respect to the imaging apparatus from said one or more structured-light images; and
   determine physical area size or physical volume size of the object of interest based on said one or more regular images and the distance information.

* * * * *